United States Patent [19]

Belletire

[11] 4,374,148

[45] Feb. 15, 1983

[54] CARBOXYLIC ACID THERAPEUTIC AGENTS

[75] Inventor: John L. Belletire, Cincinnati, Ohio

[73] Assignee: Pfizer Inc., New York, N.Y.

[21] Appl. No.: 282,762

[22] Filed: Jul. 13, 1981

Related U.S. Application Data

[62] Division of Ser. No. 199,153, Oct. 21, 1980, Pat. No. 4,305,955.

[51] Int. Cl.³ .................. A61K 31/165; A61K 31/19; A61K 31/235
[52] U.S. Cl. ..................................... 424/317; 424/324
[58] Field of Search ........................ 424/308, 317, 324

[56] References Cited

U.S. PATENT DOCUMENTS 3,565,904 2/1971 Juby et al. .......................... 424/317

OTHER PUBLICATIONS

G. A. Stewart, "Pharmacological Studies on Oral Hypoglycemic Agents," Dtsch.-Eng. Med. Rundsch. (Anglo-German Medical Review), vol. 1, p. 334, (1962).

S. Ch. Lahiri et al., "Studies on Indan Acids as Potential Oral Hypoglycemic Agents," Journal of the Indian Chemical Society, vol. 53, p. 1041, (1976).

Primary Examiner—Frederick E. Waddell
Attorney, Agent, or Firm—Charles J. Knuth; Peter C. Richards

[57] ABSTRACT

A series of substituted phenylacetic acid compounds and their derivatives, including the pharmacologically acceptable base salts of said acids, have been found to be active as oral hypoglycemic agents. Preferred member compounds include 6-ethoxy-1,2,3,4-tetrahydronaphthalene-1-carboxylic acid, 6-benzyloxy-1,2,3,4-tetrahydronaphthalene-1-carboxylic acid, chroman-4-carboxylic acid, p-chlorophenylacetic acid, o-methylphenylacetic acid, o-methoxyphenylacetic acid, p-methoxyphenylacetic acid and α,α-di(4-methoxyphenyl)acetic acid. Synthetic routes leading to those member compounds which are novel per se are described in some detail.

14 Claims, No Drawings

CARBOXYLIC ACID THERAPEUTIC AGENTS

This is a division of application Ser. No. 199,153, filed on Oct. 21, 1980 now U.S. Pat. No. 4,305,955.

BACKGROUND OF THE INVENTION

This invention relates to new and useful carboxylic acid hypoglycemic agents. More particularly, it is concerned with a series of substituted phenylacetic acids and their derivatives, including the base salts of said acids with pharmacologically acceptable cations, which are useful in therapy as oral hypoglycemic agents for the treatment of diabetes. The invention also includes various novel oral pharmaceutical compositions as well as a method of therapy.

In the past, various attempts have been made by numerous investigators in the specialized field of synthetic organic medicinal chemistry to obtain new and better oral hypoglycemic agents. For the most part, these efforts have principally involved the synthesis and testing of various heretofore new and unavailable organic compounds, particularly in the area of the sulfonylureas, in an endeavor to determine their ability to lower blood sugar (i.e., glucose) levels when given by the oral route of administration. However, in the search for new and still more effective antidiabetic agents, far less is known about the effect of nonsulfonylureas and this is particularly so in the case of various carboxylic acid compounds. For instance, G. A. Stewart in *Dtsch.-Eng. Med. Rundsch.* (Anglo-German Medical Review), Vol. 1, p. 334 (1962) reports that phenylacetic acid is hypoglycemic in normal guinea pigs when given by the oral route of administration at 500 and 750 mg./kg., respectively, while S. Ch. Lahiri et al. in the Journal of the Indian Chemical Society, Vol. 53, p. 1041 (1976) have additionally found that 6-methoxyindan-1-carboxylic acid and 6-methoxyindan-1-acetic acid are both hypoglycemic in normal and alloxan-diabetic rabbits when given by the oral route of administration at dose levels in the neighborhood of 200 mg./kg., respectively. However, none of these prior art compounds possess any outstanding clinical (or even pharmacological) advantages over that of either chlorpropamide or tolbutamide when used in this connection.

SUMMARY OF THE INVENTION

In accordance with the present invention, it has now been rather surprisingly found that certain cyclic and non-cyclic phenylacetic acids are extremely useful when employed as oral hypoglycemic agents for the treatment of diabetic subjects despite the fact that they are employed at dose levels where the aforementioned prior art compounds exhibit little or no activity. More particularly, the novel oral pharmaceutical compositions of this invention all comprise a pharmaceutically acceptable carrier and an effective blood sugar lowering amount of an oral hypoglycemic agent, said agent being a compound selected from the group consisting of carboxylic acids of the formulae:

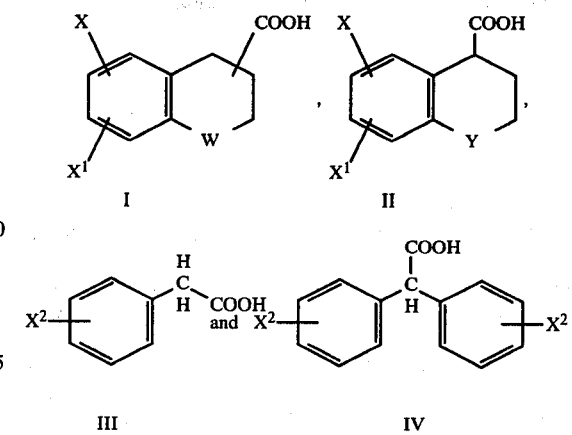

and the lower alkyl esters and unsubstituted amide derivatives thereof, and the base salts of said acids with pharmacologically acceptable cations, wherein W is $-CH_2-$ or $-CH(CH_3)-$; X is hydrogen or lower alkyl; $X^1$ is hydrogen, lower alkyl, lower alkoxy or lower phenylalkoxy, with the proviso that when $X^1$ is other than lower alkyl, X is hydrogen; $X^2$ is fluorine, chlorine, bromine, lower alkyl, lower alkoxy or lower phenylalkoxy; and Y is oxygen or sulfur. These compounds are all useful in lowering blood sugar levels when given by the oral route of administration, i.e., they are useful as oral hypoglycemic agents.

The novel compounds of this invention are those carboxylic acids of formula I where X is hydrogen and $X^1$ is other than hydrogen, methyl or methoxy, and those of formula II where at least one of X and $X^1$ is always other than hydrogen. Additionally, the carboxylic acids of formula IV are all novel compounds.

Accordingly, the novel compounds of formula I comprise 1,2,3,4-tetrahydronaphthalenecarboxylic acids of the formula:

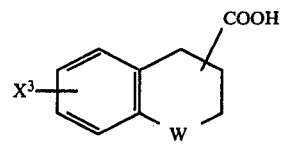

and the lower alkyl esters and unsubstituted amide derivatives thereof, and the base salts of said acids with pharmacologically acceptable cations, wherein $X^3$ is lower phenylalkoxy and W is $-CH_2-$ or $-CH(CH_3)-$.

The novel compounds of formula II comprise chroman and thiochromancarboxylic acids of the formula:

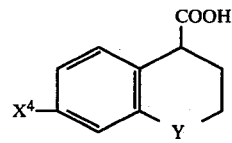

and the lower alkyl esters and unsubstituted amide derivatives thereof, and the base salts of said acids with pharmaceutically acceptable cations, wherein $X^4$ is lower alkoxy or lower phenylalkoxy and Y is oxygen or sulfur.

Lastly, the novel compounds of formula IV comprise α,α-diphenylacetic acids of the formula:

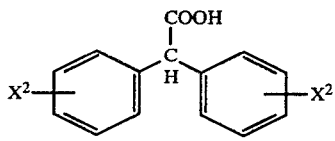

and the lower alkyl esters and unsubstituted amide derivatives thereof, and the base salts of said acids with pharmacologically acceptable cations, where $X^2$ is fluorine, chlorine, bromine, lower alkyl, lower alkoxy or lower phenylalkoxy.

Of especial interest in this connection are such typical and preferred member compounds of the invention as 4-methyl-1,2,3,4-tetrahydronaphthalene-1-carboxylic acid, 6-methoxy-1,2,3,4-tetrahydronaphthalene-1-carboxylic acid, 6-ethoxy-1,2,3,4-tetrahydronaphthalene-1-carboxylic acid, 6-benzyloxy-1,2,3,4-tetrahydronaphthalene-1-carboxylic acid, chroman-4-carboxylic acid, thiochroman-4-carboxylic acid, p-chlorophenylacetic acid, o-methylphenylacetic acid, o-methoxyphenylacetic acid, p-methoxyphenylacetic acid and α,α-di(4-methoxyphenyl)acetic acid, respectively. These particular compounds are all highly potent as regards their hypoglycemic activity (i.e., they exhibit a marked improvement in glucose tolerance). The preferred 6-substituted-1,2,3,4-tetrahydronaphthalene-1-carboxylic acids where the 6-substituent is other than methoxy, as well as thiochroman-4-carboxylic acid and α,α-di(4-methoxyphenyl)acetic acid are, as previously indicated, new compounds per se.

DETAILED DESCRIPTION OF THE INVENTION

In accordance with the process employed for preparing the compounds of this invention of structural formulae I-II and IV as previously defined, an appropriately substituted ketone compound, such as the corresponding 1-tetralone, 2-tetralone, 4-chromanone, thiochroman-4-one and symmetrically disubstituted benzophenone, of the respective formulae:

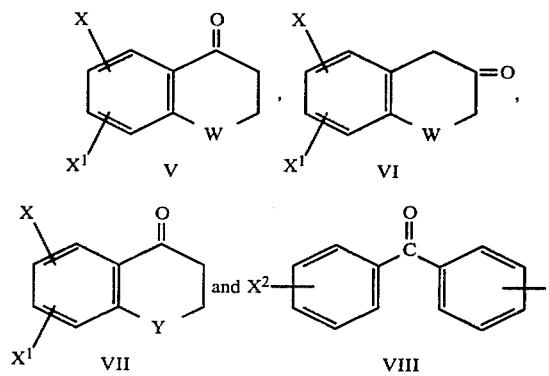

wherein W, X, $X^1$, $X^2$ and Y are all as previously defined, is treated with a suitable trialkylsilyl cyanide to form the corresponding cyanotrialkylsilyloxy derivative, followed by reductive hydrolysis of the latter intermediate to yield the desired acid. A preferred trialkylsilyl cyanide for use in this connection is trimethylsilyl cyanide, although any lower trialkylsilyl cyanide having up to four carbon atoms in each alkyl moiety may be employed in the aforesaid addition reaction. In general, this particular reaction is normally carried out in the presence of a Lewis acid catalyst, such as a zinc or aluminum halide (like zinc iodide) or boron trifluoride, with zinc iodide being the preferred catalyst for the present purposes at hand. Moreover, the reaction is conducted at a temperature that is in the range of from about 0° C. up to about 50° C. (with the preferred temperature range being 0°-20° C.) either neat or in a reaction-inert organic solvent, such as diethyl ether, dimethoxyethane, tetrahydrofuran, dioxane and the like, and it is usually conducted in an inert atmosphere, preferably one that is nitrogen. The cyano trialkylsiloxy derivative so obtained is then converted to the desired carboxylic acid compound by simply treating said cyano ether with a stannous halide salt, such as stannous chloride dihydrate, for example, in a concentrated acid mix such as a mixture of glacial acetic acid and concentrated hydrochloric acid. The latter reaction (i.e., the reductive hydrolysis step) is usually conducted at a temperature that is in the range of from about 100° C. up to about 200° C. (and preferably at the reflux point) for a period of about 12 to 72 hours. Upon completion of the reaction, the desired product (i.e., the carboxylic acid final product having the requisite structural formula) is easily isolated in a conventional manner and used as such or else simply converted to a suitable derivative thereof as will hereinafter be more fully described.

Needless to say, compounds of the invention of structural formula III can also be prepared by using the hereinbefore described two-step reaction process for synthesizing the cyclic and non-cyclic phenylacetic acid compounds, only this time employing an appropriately substituted aldehyde compound as starting material in place of the corresponding ketone substrate (see structural formula VIII). However, many of the compounds of structural formula III are commercially available or else can be prepared by simpler routes well-known to those skilled in the art. On the other hand, certain compounds of the invention (of structural formulae I-IV) having a ring substituent ($X^1$, $X^2$) which is lower alkoxy of more than one carbon atom or lower phenylalkoxy are novel per se and can alternatively be prepared from the corresponding methoxy compounds by first converting same to the corresponding hydroxy derivatives and then alkylating the latter with the appropriate agent of choice (e.g., ethyl iodide or benzyl bromide, as the case may be) in a manner well known to those skilled in the art. As previously indicated, all these acid compounds (of structural formula III and so on) can be used as such for the present purposes at hand or else simply converted to the corresponding lower alkyl ester and unsubstituted amide derivatives thereof in accordance with conventional techniques.

The lower alkyl esters of the non-aromatic carboxylic acids of this invention are generally prepared by condensation of the acid with the appropriate alcohol of choice in the presence of an acid catalyst in accordance with conventional organic procedure. The unsubstituted amide derivatives, on the other hand, are readily prepared by using standard procedures, for example, by treating the corresponding acid chloride with ammonia under basic conditions and thereafter isolating the amide final product in the usual manner.

The ketone starting materials (of structural formulae V-VIII) required for preparing the carboxylic acid compounds of this invention are, for the most part, known compounds and are either readily available commercially, like 1-tetralone, 4-methyl-1-tetralone, 5-methoxy-1-tetralone, 6-methoxy-1-tetralone, 4-chromanone, thiochroman-4-one and 4,4'-dimethoxybenzophenone, etc., or else they can easily be synthesized by those skilled in the art starting from common chemical reagents and using conventional methods of organic synthesis already described in the literature. As previously indicated, the carboxylic acid final products of structural formula III are, for the most part, known phenylacetic acids many of which are commercially available.

The chemical bases which are used as reagents in this invention to prepare the aforementioned pharmaceutically acceptable base salts are those which form non-toxic salts with the various herein described carboxylic acid compounds, such as 6-benzyloxy-1,2,3,4-tetrahydronaphthalene-1-carboxylic acid, for example. These particular non-toxic base salts are of such a nature that their cations are said to be essentially non-toxic in character over the wide range of dosage administered. Examples of such cations include those of sodium, potassium, calcium and magnesium, etc. These salts can easily be prepared by simply treating the aforementioned carboxylic acids with an aqueous solution of the desired pharmacologically acceptable cation, and then evaporating the resulting solution to dryness while preferably being placed under reduced pressure. Alternatively, they may also be prepared by mixing lower alkanolic solutions of the said acidic compounds and the desired alkali metal alkoxide together, and then evaporating the resulting solution to dryness in the same manner as before. In either case, stoichiometric quantities of reagents must be employed in order to ensure completeness of reaction and maximum production of yields with respect to the desired final product.

As previously indicated, the carboxylic acid compounds of this invention are all readily adapted to therapeutic use as oral hypoglycemic agents, in view of their ability to lower the blood sugar levels of both diabetic and non-diabetic subjects to a substantially significant degree. For instance, 6-ethoxy-1,2,3,4-tetrahydronaphthalene-1-carboxylic acid, a typical and preferred agent of the present invention, has been found to consistently lower blood sugar levels in the fasted, glucose-loaded rat to a statistically significant degree when given by the intraperitoneal route of administration at a dose level of 100 mg./kg. without showing any substantial signs of toxic side effects. The other compounds of this invention can also be administered in this manner without causing any significant untoward pharmacological side reactions. In general, these compounds are ordinarily administered at dosage levels ranging from about 0.2 mg. to about 25 mg. per kg. of body weight per day, although variations will necessarily occur depending upon the condition and individual response of the subject being treated and the particular type of oral pharmaceutical formulation chosen.

The carboxylic acid compounds of this invention may be administered either alone or in combination with pharmaceutically acceptable carriers and such administration can be carried out in both single and multiple dosages. More particularly, the compounds of the invention can be administered in a wide variety of different dosage forms, i.e., they may be combined with various pharmaceutically acceptable inert carriers in the forms of tablets, capsules, lozenges, troches, hard candies, powders, aqueous suspension, elixirs, syrups and the like. Such carriers include solid diluents or fillers, sterile aqueous media and various non-toxic organic solvents, etc. Moreover, such oral pharmaceutical compositions can be suitably sweetened and/or flavored by means of various agents of the type commonly employed for just such a purpose. In general, the therapeutically-effective compounds of this invention are present in such dosage forms at concentration levels ranging from about 0.5% to about 90% by weight of the total composition, i.e., in amounts which are sufficient to provide the desired unit dosage.

For purposes of oral administration, tablets containing various excipients such as sodium citrate, calcium carbonate and dicalcium phosphate may be employed along with various disintegrants such as starch and preferably potato or tapioca starch, alginic acid and certain complex silicates, together with binding agents such as polyvinylpyrrolidone, gelatin and acacia. Additionally, lubricating agents such as magnesium stearate, sodium lauryl sulfate and talc are often very useful for tabletting purposes. Solid compositions of a similar type may also be employed as fillers in soft and hard-filled gelatin capsules; preferred materials in this connection also include the high molecular weight polyethylene glycols. When aqueous suspensions and/or elixirs are desired for oral administration, the essential active ingredient therein may be combined with various sweetening or flavoring agents, coloring matter or dyes and, if so desired, emulsifying and/or suspending agents as well, together with such diluents as water, ethanol, propylene glycol, glycerin and various like combinations thereof.

The activity of the compounds of the present invention, as hypoglycemic agents, is determined by their ability to lower blood sugar levels in the fasted rat when tested therein for such purposes according to the procedure described by W. S. Hoffman, as reported in the *Journal of Biological Chemistry*, Vol. 120, p. 51 (1937). The latter method measures directly the amount of glucose in the blood at any given time and from this, the maximum percent decrease in blood sugar can be readily calculated. In this way, the present carboxylic acid final products are shown to markedly reduce the blood sugar levels of non-anesthetized, glucose-loaded rats when administered to them at dose levels as low as 100 mg./kg.

PREPARATION A

To a single-neck, round-bottomed reaction flask equipped with a magnetic stirrer, a 50 ml. pressure equalizing addition funnel and a nitrogen-inlet tube, there were added 10.0 g. (0.0567 mole) of 6-methoxy-1-tetralone (available from the Aldrich Chemical Company, Inc., Milwaukee, Wis.) and 0.35 g. of anhydrous zinc iodide. The addition funnel was then charged with 19.0 g. (0.191 mole) of trimethylsilyl cyanide and the reaction apparatus flushed with dry nitrogen. Vigorous stirring of the reaction mixture then commenced, while the trimethylsilyl cyanide was added over a period of five minutes causing a modest exotherm. The resulting warm mixture was next stirred under a dry nitrogen atmosphere for a period of 48 hours at ambient temperatures. Work-up of the spent mixture was then achieved by dilution of same with 300 ml. of chloroform, followed by washing of the organic layer (three times) with saturated aqueous sodium bicarbonate. After removal of the drying agent by means of filtration and the organic solvent by means of evaporation under reduced pressure, there were finally obtained 13 g. (83%) of pure 6-methoxy-1-cyano-1-trimethylsilyloxy-1,2,3,4-tetrahydronaphthalene, m.p. 66°–67° C. after recrystallization from n-hexane. The yield of analytically pure material (m.p. 66°–67° C.) amounted to 10.0 g. (64%).

Anal. Calcd. for $C_{15}H_{21}O_2Si$: C, 65.41; H, 7.68; N, 5.08. Found: C, 65.61; H, 7.68; N, 5.46.

To a 250 ml. single-neck, round-bottomed reaction flask equipped with a magnetic stirrer, reflux condenser and nitrogen-inlet tube, there were added 6.0 g. (0.02179 mole) of 6-methoxy-1-cyano-1-trimethylsilyloxy-1,2,3,4-tetrahydronaphthalene, followed by the addition of 20.0 g. (0.0886 mole) of stannous chloride dihydrate in one portion and then 20 ml. of glacial acetic acid and 20 ml. of concentrated hydrochloric acid shortly thereafter. The reaction apparatus was then immediately flushed with dry nitrogen and plunged into a preheated oil bath at 140° C. Vigorous stirring of the reaction mixture was then maintained, while it was slowly heated at the reflux point for a period of 65 hours. The resulting mixture was then cooled to room temperature (~25° C.), diluted with 250 ml. of chloroform and the separated organic layer subsequently removed therefrom. The remaining aqueous phase was again saturated with chloroform and the combined organic layers thereafter extracted with three-75 ml. portions of 2 N aqueous potassium hydroxide, followed by back extraction of the resulting combined aqueous layers with one-75 ml. portion of diethyl ether. The basic aqueous layer which separated was then saved and subsequently acidified with concentrated hydrochloric acid (with the aid of icebath cooling), followed by extraction of the acidified mixture with three-separate 250 ml. portions of chloroform. The combined chloroform extracts were then dried over anhydrous magnesium sulfate and filtered, and the resulting clear filtrate was thereafter concentrated in vacuo to ultimately afford pure 6-methoxy-1,2,3,4-tetrahydronaphthalene-1-carboxylic acid as a crystalline residue. The yield of pure material amounted to 3.017 g. (67%). Kugelrohr distillation at 110°–180° C./0.5 mm. Hg then gave analytically pure product. In this way, there were finally obtained 2.91 g. (65%) of analytically pure 6-methoxy-1,2,3,4-tetrahydronaphthalene-1-carboxylic acid, m.p. 88°–89° C. [literature m.p. 96°–97° C., according to C. C. Price et al., in the *Journal of the American Chemical Society*, Vol. 69, p. 2261 (1977)].

Anal. Calcd. for $C_{12}H_{14}O_3$: C, 69.88; H, 6.84. Found: C, 69.82; H, 6.73.

PREPARATION B

The two-step procedure described in Preparation A was repeated except that 1-tetralone (available from the Aldrich Chemical Company, Inc., Milwaukee, Wis.) was the ultimate starting material employed in place of 6-methoxy-1-tetralone, using the same molar proportions as before. In this particular case, the corresponding final product obtained was 1,2,3,4-tetrahydronaphthalene-1-carboxylic acid, m.p. 82°–83° C. [literature m.p. 84°–86° C., according to R. W. Kay et al., in the *Journal of the Chemical Society*, Vol. 105, p. 1571 (1914)]. The yield of pure product was 68% of the theoretical value.

Anal. Calcd. for $C_{11}H_{12}O_2$: C, 74.98; H, 6.86. Found: C, 74.77; H, 6.91.

PREPARATION C

The two-step procedure described in Preparation A was repeated except that 4-methyl-1-tetralone (available from the Aldrich Chemical Company, Inc., Milkaukee, Wis.) was the ultimate starting material employed in place of 6-methoxy-1-tetralone, using the same molar proportions as before. In this particular case, the corresponding final product obtained was 4-methyl-1,2,3,4-tetrahydronaphthalene-1-carboxylic acid [a viscous oil, first reported in *Chemical Abstracts*, Vol. 67, p. 63169R (1966)]. The yield of pure product was 58% of the theoretical value.

Anal. Calcd. for $C_{12}H_{14}O_2$: C, 75.76; H, 7.42. Found: C, 75.71; H, 7.34.

PREPARATION D

The two-step procedure described in Preparation A was repeated except that 4-chromanone (available from the Aldrich Chemical Company, Inc., Milwaukee, Wis.) was the ultimate starting material employed in place of 6-methoxy-1-tetralone, using the same molar proportions as before. In this particular case, the corresponding final product obtained was chroman-4-carboxylic acid, m.p. 90°–91.5° C. [literature m.p. 66° C., according to G. Fontaine in *Annales de chimie*, Vol. 3, p. 179 (1968)]. The yield of pure product was 77% of the theoretical value.

Anal. Calcd. for $C_{10}H_{10}O_3$: C, 67.40; H, 5.66. Found: C, 67.37; H, 5.55.

PREPARATION E

6-Methoxy-1,2,3,4-tetrahydronaphthalene-2-carboxylic acid was prepared according to the procedure described by Jacques et al., in the *Bulletin de la Societe chimique de France*, p. 512 (1950), starting from readily available materials. The product obtained was identical in every respect with the prior art compound.

PREPARATION F p-Chlorophenylacetic acid is commercially available and was obtained from the Aldrich Chemical Company, Inc. of Milwaukee, Wis.

PREPARATION G o-Methylphenylacetic acid is commercially available and was obtained from Pfaltz & Bauer, Inc. of Stamford, Conn.

PREPARATION H o-Methoxyphenylacetic acid is commercially available and was obtained from the Distillation Products Industries division of the Eastman Kodak Company of Rochester, N.Y.

PREPARATION I p-Methoxyphenylacetic acid is commercially available and was obtained from the Distillation Products Industries division of the Eastman Kodak Company of Rochester, N.Y.

EXAMPLE 1

The two-step procedure described in Preparation A was repeated except that 5-methoxy-1-tetralone (available from the Aldrich Chemical Company, Inc., Milwaukee, Wis.) was the ultimate starting material employed in place of 6-methoxy-1-tetralone, using the same molar proportions as before. In this particular case, the corresponding final product obtained was 5-methoxy-1,2,3,4-tetrahydronaphthalene-1-carboxylic acid, m.p. 96°–97° C. The yield of pure product was 39% of the theoretical value.

Anal. Calcd. for $C_{12}H_{14}O_3$: C, 69.88; H, 6.84. Found: C, 70.08; H, 6.72.

EXAMPLE 2

The two-step procedure described in Preparation A was repeated except that 6,7-dimethyl-4-chromanone [*Chemical Abstracts,* Vol. 58, p. 13900c (1964)] was the ultimate starting material employed in place of 6-methoxy-1-tetralone, using the same molar proportions as before. In this particular case, the corresponding final product obtained was 6,7-dimethylchroman-4-carboxylic acid, m.p. 154°–155° C. after recrystallization from cyclohexane. The yield of pure product was 92% of the theoretical value.

Anal. Calcd. for $C_{12}H_{14}O_3$: C, 69.88; H, 6.84. Found: C, 69.89; H, 6.87.

EXAMPLE 3

The two-step procedure described in Preparation A was repeated except that 7-methoxy-4-chromanone (British Pat. No. 1,024,645) was the ultimate starting material employed in place of 6-methoxy-1-tetralone, using the same molar proportions as before. In this particular case, the corresponding final product obtained was 7-methoxychroman-4-carboxylic acid, m.p. 64°–67° C. The yield of pure product was 35% of the theoretical value.

Anal. Calcd. for $C_{11}H_{12}O_4$: C, 63.45; H, 5.81. Found: C, 63.16; H, 5.73.

EXAMPLE 4

The two-step procedure described in Preparation A was repeated except that thiochroman-4-one (available from Pfaltz & Bauer, Inc. of Stamford, Conn.) was the ultimate starting material employed in place of 6-methoxy-1-tetralone, using the same molar proportions as before. In this particular case, the corresponding final product obtained was thiochroman-4-carboxylic acid, m.p. 78°–80° C. The yield of pure product was 71% of the theoretical value.

Anal. Calcd. for $C_{10}H_{10}O_2S$: C, 61.83; H, 5.19. Found: C, 62.09; H, 5.14.

EXAMPLE 5

The two-step procedure described in Preparation A was repeated except that 4,4'-dimethoxybenzophenone (available from the Aldrich Chemical Company, Inc., Milwaukee, Wis.) was the ultimate starting material employed in place of 6-methoxy-1-tetralone, using the same molar proportions as before. In this particular case, the corresponding final product obtained was α,α-di(4-methoxyphenyl)acetic acid, m.p. 110°–112° C. The yield of pure product was 24% of the theoretical value.

Anal. Calcd. for $C_{16}H_{16}O_4$: C, 70.57; H, 5.95. Found: C, 70.45; H, 5.85.

EXAMPLE 6

A mixture consisting of 5.9 g. (0.029 mole) of 6-methoxy-1,2,3,4-tetrahydronaphthalene-1-carboxyllic acid (prepared as described in Preparation A), 100 ml. of glacial acetic acid and 100 ml. of 48% hydrobromic acid was refluxed for a period of six hours. At the end of this time, the spent reaction mixture was cooled to room temperature (~25° C.) and then poured onto ice, followed by extraction of the resulting aqueous mass with ethyl acetate. After washing the latter organic solution with water and drying over anhydrous magnesium sulfate, the resulting clear solution was filtered and subsequently evaporated to near dryness while under reduced pressure to afford a crystalline mass as residue. Recrystallization of the latter material from chloroform/n-hexane then gave 3.4 g. (59%) of pure 6-hydroxy-1,2,3,4-tetrahydronaphthalene-1-carboxylic acid, m.p. 133°–134° C. A second crystalline crop subsequently yielded 740 mg. of pure material (m.p. 132°–133° C.). The pure product was further characterized by means of mass spectroscopy (m/e, 192).

EXAMPLE 7

A solution consisting of 1.4 g. (0.007 mole) of 6-hydroxy-1,2,3,4-tetrahydronaphthalene-1-carboxylic acid (prepared as described in Example 6) dissolved in 35 ml. of dry tetrahydrofuran was treated with 672 mg. of 50% sodium hydride (dispersed in mineral oil) at 0° C., while under a dry nitrogen atmosphere. The resulting suspension was then stirred at room temperature (~25° C.) for a period of 30 minutes, followed by refluxing for a period of one hour. At this point, 1.09 g. (0.007 mole) of ethyl iodide was added dropwise to the stirred mixture, followed by further refluxing for a period of 15 minutes and then the addition of 3 ml. of dimethylsulfoxide. The resulting reaction solution was then refluxed for a period of two hours and finally allowed to cool to room temperature. The spent reaction mixture was next stirred at room temperature and thereafter was immediately treated with 10 ml. of water in a dropwise fashion, followed by the addition of further water to form a diluted aqueous system. The latter system was then extracted with ethyl acetate and the resulting organic layer separated, while the resulting aqueous phase was saved and subsequently adjusted to pH 4.5 with 6 N hydrochloric acid. The acidified aqueous system was next extracted with ethyl acetate, and the resulting organic layers were combined and subsequently washed well with water and dried over anhydrous sodium sulfate. After removal of the drying agent by means of filtration and the solvent by means of evaporation under reduced pressure, there was obtained a residue which was subsequently chromatographed on silica gel using chloroform/methanol (9:1 by volume) as the eluant. Recrystallization of the major fraction from n-hexane then gave 750 mg. (49%) of pure 6-ethoxy-1,2,3,4-tetrahydronaphthalene-1-carboxylic acid, m.p. 109°–111° C.

Anal. Calcd. for $C_{13}H_{16}O_3$: C, 70.89; H, 7.32. Found: C, 70.99; H, 7.38.

EXAMPLE 8

The procedure described in Example 7 was repeated except that benzyl bromide was the alkylating agent of choice employed instead of ethyl iodide, using the same molar proportions as before. In this particular case, the corresponding final product obtained was 6-benzyloxy-1,2,3,4-tetrahydronaphthalene-1-carboxylic acid, m.p. 88°–92° C. The yield of pure product was 46% of the theoretical value.

Anal. Calcd. for $C_{18}H_{18}O_3$: C, 76.57; H, 6.43. Found: C, 76.32; H, 6.38.

EXAMPLE 9

The following carboxylic acid compounds are prepared by employing the procedures previously described in Examples 1–8 (as well as Preparations A–D), starting from readily available materials in each instance:

5-isopropyl-1,2,3,4-tetrahydronaphthalene-1-carboxylic acid
6-methyl-1,2,3,4-tetrahydronaphthalene-1-carboxylic acid
7-(n-butyl)-1,2,3,4-tetrahydronaphthalene-1-carboxylic acid
5-hydroxy-1,2,3,4-tetrahydronaphthalene-1-carboxylic acid
5-ethoxy-1,2,3,4-tetrahydronaphthalene-1-carboxylic acid
6-(n-butoxy)-1,2,3,4-tetrahydronaphthalene-1-carboxylic acid
6,7-diethyl-1,2,3,4-tetrahydronaphthalene-1-carboxylic acid
5-benzyloxy-1,2,3,4-tetrahydronaphthalene-1-carboxylic acid
6-(β-phenylethoxy)-1,2,3,4-tetrahydronaphthalene-1-carboxylic acid
1,2,3,4-tetrahydronaphthalene-2-carboxylic acid
4-methyl-1,2,3,4-tetrahydronaphthalene-2-carboxylic acid
6-hydroxy-1,2,3,4-tetrahydronaphthalene-2-carboxylic acid
6-benzyloxy-1,2,3,4-tetrahydronaphthalene-2-carboxylic acid
4-methyl-6-hydroxy-1,2,3,4-tetrahydronaphthalene-2-carboxylic acid
4-methyl-6-benzyloxy-1,2,3,4-tetrahydronaphthalene-2-carboxylic acid
6-methoxychroman-4-carboxylic acid
6,8-dimethylchroman-4-carboxylic acid
6-(n-butyl)chroman-4-carboxylic acid
7-methylchroman-4-carboxylic acid
7-hydroxychroman-4-carboxylic acid
7-(n-butoxy)chroman-4-carboxylic acid
7-benzyloxychroman-4-carboxylic acid
6,8-di(n-butyl)chroman-4-carboxylic acid
7-methoxythiochroman-4-carboxylic acid
7-hydroxythiochroman-4-carboxylic acid
7-benzyloxythiochroman-4-carboxylic acid
6-methylthiochroman-4-carboxylic acid
7-(n-butyl)thiochroman-4-carboxylic acid
7-(n-butoxy)thiochroman-4-carboxylic acid
6-methoxythiochroman-4-carboxylic acid
6,7-dimethylthiochroman-4-carboxylic acid
6,8-di(n-butyl)thiochroman-4-carboxylic acid
7-(β-phenylethoxy)thiochroman-4-carboxylic acid
α,α-di(2-fluorophenyl)acetic acid
α,α-di(4-chlorophenyl)acetic acid
α,α-di(3-chlorophenyl)acetic acid
α,α-di(3-bromophenyl)acetic acid
α,α-di(2-methylphenyl)acetic acid
α,α-di(4-isobutylphenyl)acetic acid
α,α-di(3-ethoxyphenyl)acetic acid
α,α-di(4-hydroxyphenyl)acetic acid
α,α-di(4-isopropoxyphenyl)acetic acid
α,α-di(4-benzyloxyphenyl)acetic acid

EXAMPLE 10

A solution consisting of 2.82 g. (0.01 mole) of pure 6-benzyloxy-1,2,3,4-tetrahydronaphthalene-1-carboxylic acid (prepared according to the procedure described in Example 8) dissolved in 100 ml. of ethanol is saturated with dry hydrogen chloride gas, and the resultant mixture is then refluxed for a period of approximately four hours. Upon completion of this step, the solvent is removed by means of evaporation under reduced pressure and the residue subsequently make alkaline by the addition thereto of a saturated aqueous sodium bicarbonate solution. The resulting solution is then extracted with diethyl ether, and the combined ethereal extracts are subsequently dried over anhydrous sodium sulfate and filtered. After removal of the drying agent by means of filtration and the solvent in the usual manner, there is obtained crude ester product in the form of a solid crystalline residue. Recrystallization of the latter material from ethanol then affords the pure ethyl ester of 6-benzyloxy-1,2,3,4-tetrahydronaphthalene-1-carboxylic acid in substantial yield.

EXAMPLE 11

The procedure described in Example 10 is repeated except for the fact that methanol is the reagent employed instead of ethanol and the methyl ester of 6-benzyloxy-1,2,3,4-tetrahydronaphthalene-1-carboxylic acid is the corresponding final product thus obtained.

In like manner, the n-propyl, isopropyl, n-butyl, isobutyl, n-amyl, isoamyl and n-hexyl esters of 6-benzyloxy-1,2,3,4-tetrahydronaphthalene-1-carboxylic acid are also similarly prepared by merely employing the appropriate alcohol of choice in place of ethanol in each particular case.

EXAMPLE 12

The procedure described in Example 10 is repeated except that 7-methoxychroman-4-carboxylic acid (prepared according to the procedure described in Example 3) is the starting material employed in place of 6-benzyloxy-1,2,3,4-tetrahydronaphthalene-1-carboxylic acid for the present purposes at hand. In this particular case, the corresponding final product thus obtained is the ethyl ester of 7-methoxychroman-4-carboxylic acid.

In like manner, the methyl, n-propyl, isopropyl, n-butyl, isobutyl, n-amyl, isoamyl and n-hexyl esters of 7-methoxychroman-4-carboxylic acid are also each similarly prepared, as are the corresponding lower alkyl esters of the other carboxylic acids of this invention which are reported in Examples 1-2, 4-7 and 9, respectively.

EXAMPLE 13

A mixture of 1.41 g. (0.005 mole) of 6-benzyloxy-1,2,3,4-tetrahydro-1,2,3,4-naphthalene-1-carboxylic acid and 10 ml. of thionyl chloride dissolved in 300 ml. of chloroform is refluxed for a period of approximately 2.5-4 hours. After cooling to room temperature (~25° C.), the reaction mixture is slowly poured into a solution consisting of 4.5 g. of sodium hydroxide dissolved in 100 ml. of ammonium hydroxide. The resulting chloroform layer is then separated and subsequently evaporated to near dryness while under reduced pressure to give a residual solid. Recrystallization of the latter material from ethanol-water then yields pure 6-benzyloxy-1,2,3,4-tetrahydronaphthalene-1-carboxamide in fine crystalline form.

EXAMPLE 14

The procedure described in Example 13 is repeated except that 7-methoxychroman-4-carboxylic acid is the starting material employed in place of 6-benzyloxy-1,2,3,4-tetrahydronaphthalene-1-carboxylic acid for the present purposes at hand. In this particular case, the corresponding final product thus obtained is 7-methoxy-chroman-4-carboxamide.

In like manner, the unsubstituted amides of the other carboxylic acids of this invention are also similarly prepared by merely employing the appropriate acid starting material of choice (taken from Examples 1-2, 4-7 and 9, respectively) in each particular case.

EXAMPLE 15

The sodium salt of 6-benzyloxy-1,2,3,4-tetrahydronaphthalene-1-carboxylic acid is prepared by dissolving said acid in water containing an equivalent amount in moles of sodium hydroxide and then freeze-drying the mixture. In this way, the desired alkali metal salt of the carboxylic acid is obtained in the form of an amorphous powder which is freely-soluble in water.

In like manner, the potassium and lithium salts are also similarly prepared, as are the other alkali metal salts of all the other carboxylic acids of this invention which are reported in Examples 1-7 and 9, respectively.

EXAMPLE 16

The calcium salt of 7-methoxychroman-4-carboxylic acid is prepared by dissolving said acid in water containing an equivalent amount in moles of calcium hydroxide and then freeze-drying the mixture. The corresponding magnesium salt is also prepared in this manner, as are all the other alkaline-earth metal salts not only of this particular compound, but also of those carboxylic acids previously described in Examples 1-2 and 4-9, respectively.

EXAMPLE 17

A dry solid pharmaceutical composition is prepared by blending the following materials together in the proportions by weight specified below:

| | |
|---|---|
| 6-Benzyloxy-1,2,3,4-tetrahydronaphthalene-1-carboxylic acid | 50 |
| Sodium citrate | 25 |
| Alginic acid | 10 |
| Polyvinylpyrrolidone | 10 |
| Magnesium stearate | 5 |

After the dried composition is thoroughly blended, tablets are punched from the resulting mixture, each tablet being of such size that it contains 200 mg. of the active ingredient. Other tablets are also prepared in a similar fashion containing 25, 50 and 100 mg. of the action ingredient, respectively, by merely using the appropriate amount of the carboxylic acid compound in each case.

EXAMPLE 18

A dry solid pharmaceutical composition is prepared by combining the following materials together in the proportions by weight indicated below:

| | |
|---|---|
| α,α-Di(4-methoxyphenyl)acetic acid | 50 |
| Calcium carbonate | 20 |
| Polyethylene glycol, average molecular weight 4000 | 30 |

The dried weight solid mixture so prepared is then thoroughly agitated so as to obtain a powdered product that is completely uniform in every respect. Soft elastic and hard-filled gelatin capsules containing this pharmaceutical composition are then prepared, employing a sufficient quantity of material in each instance so as to provide each capsule with 250 mg. of the active ingredient.

EXAMPLE 19

The following carboxylic acid final products of Preparations A-I and Examples 3-5 and 7-8, respectively, were tested for hypoglycemic activity in terms of their ability to exhibit improved glucose tolerance in groups of five or six male albino rats (each weighing approximately 200-255 g.) of the Charles River strain. No anesthetic was used in this study. The rats were fasted for approximately 18-24 hours prior to administration, a blood sample (zero time) was taken from the tail vein of each animal (having cut at a point just 2 mm. from the tip of the tail) and each animal so examined was thereafter treated with glucose at a dose level of 1.0 g./kg. (made up in 0.9% saline), via the intraperitoneal route of administration, followed by treatment with either saline alone (controls) or the test compound to be administered at a dose level of 100 mg./kg., also by the intraperitoneal route of administration. Additional blood samples were then taken from the tail vein in the same manner as before at 0.5, 1, 2 and 3 hour intervals after administration of the drug. The samples were immediately diluted 1:10 (by volume) with 0.1% heparin in 0.9% saline. Blood glucose concentrations (mg./dl.) were then determined by adapting the method of W. S. Hoffman [*Journal of Biological Chemistry*, Vol. 120, p. 51 (1937)] to the Autoanalyzer instrument produced by Technicon Instruments Corporation of Chauncey, N.Y. On this basis, the maximum percent decrease in blood glucose was calculated and reported as such (i.e., as hypoglycemic activity in terms of improved glucose tolerance) for the various compounds listed in the table below:

| Compound | Max. % Decrease Blood Glucose |
|---|---|
| Product of Preparation A | 17 |
| Product of Preparation B | 12 |
| Product of Preparation C | 16 |
| Product of Preparation D | 18 |
| Product of Preparation E | 13 |
| Product of Preparation F | 25 |
| Product of Preparation G | 20 |
| Product of Preparation H | 27 |
| Product of Preparation I | 32 |
| Product of Example 1 | 15 |
| Product of Example 2 | 14 |
| Product of Example 3 | 11 |
| Product of Example 4 | 15 |
| Product of Example 5 | 18 |
| Product of Example 7 | 22 |
| Product of Example 8 | 18 |

I claim:

1. A pharmaceutical composition suitable for oral administration comprising a pharmaceutically acceptable carrier and an effective blood sugar lowering amount of an oral hypoglycemic agent, said agent being a compound selected from the group consisting of carboxylic acids of the formula:

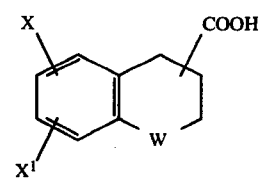

and the lower alkyl esters and unsubstituted amide derivatives thereof, and the base salts of said acids with pharmacologically acceptable cations, wherein W is —CH$_2$— or —CH(CH$_3$)—;
X is hydrogen or lower alkyl; and
X$^1$ is hydrogen, lower alkyl, lower alkoxy or lower phenylalkoxy, with the proviso that when X$^1$ is other than lower alkyl, X is hydrogen.

2. The composition as claimed in claim 1 wherein X and X$^1$ are each hydrogen and W is —CH$_2$—.

3. The composition as claimed in claim 1 wherein X is hydrogen, X$^1$ is lower alkoxy and W is —CH$_2$—.

4. The composition as claimed in claim 1 wherein X is hydrogen, X$^1$ is lower phenylalkoxy and W is —CH$_2$—.

5. The composition as claimed in claim 1 wherein X and X$^1$ are each hydrogen and W is —CH(CH$_3$)—.

6. The composition as claimed in claim 3 wherein the hypoglycemic agent is 6-methoxy-1,2,3,4-tetrahydronaphthalene-1-carboxylic acid.

7. The composition as claimed in claim 3 wherein the hypoglycemic agent is 6-methoxy-1,2,3,4-tetrahydronaphthalene-2-carboxylic acid.

8. The composition as claimed in claim 3 wherein the hypoglycemic agent is 6-ethoxy-1,2,3,4-tetrahydronaphthalene-1-carboxylic acid.

9. The composition as claimed in claim 4 wherein the hypoglycemic agent is 6-benzyloxy-1,2,3,4-tetrahydronaphthalene-1-carboxylic acid.

10. A method for lowering blood sugar in the treatment of a diabetic host, which comprises orally administering to said host an effective blood sugar lowering amount of a compound selected from the group consisting of carboxylic acids of the formula:

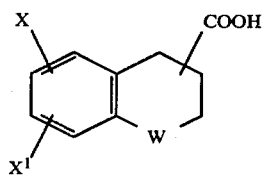

and the lower alkyl esters and unsubstituted amide derivatives thereof, and the base salts of said acids with pharmacologically acceptable cations, wherein W is —CH$_2$— or —CH(CH$_3$)—;
X is hydrogen or lower alkyl; and
X$^1$ is hydrogen, lower alkyl, lower alkoxy or lower phenylalkoxy, with the proviso that when X$^1$ is other than lower alkyl, X is hydrogen.

11. The method as claimed in claim 10 wherein the compound administered is 4-methyl-1,2,3,4-tetrahydronaphthalene-1-carboxylic acid.

12. The method as claimed in claim 10 wherein the compound administered is 6-methoxy-1,2,3,4-tetrahydronaphthalene-1-carboxylic acid.

13. The method as claimed in claim 10 wherein the compound administered is 6-ethoxy-1,2,3,4-tetrahydronaphthalene-1-carboxylic acid.

14. The method as claimed in claim 10 wherein the compound administered is 6-benzyloxy-1,2,3,4-tetrahydronaphthalene-1-carboxylic acid.

* * * * *